United States Patent [19]

Kump

[11] Patent Number: 5,053,510
[45] Date of Patent: Oct. 1, 1991

[54] PROCESS FOR THE PREPARATION OF POLYCYCLIC COMPOUNDS

[75] Inventor: Wilhelm Kump, Biel-Benken, Switzerland

[73] Assignee: Ciba-Geigy Corporation, Ardsley, N.Y.

[21] Appl. No.: 510,753

[22] Filed: Apr. 18, 1990

[30] Foreign Application Priority Data

Apr. 26, 1989 [CH] Switzerland .................. 1595/89

[51] Int. Cl.$^5$ .................................. C07D 521/00
[52] U.S. Cl. .............................. 544/368; 540/468
[58] Field of Search ..................... 540/468; 544/368

[56] References Cited

FOREIGN PATENT DOCUMENTS 350445 1/1990 European Pat. Off. ............ 544/368
WO87/3834 10/1988 World Int. Prop. O. .......... 544/368

Primary Examiner—Robert T. Bond
Attorney, Agent, or Firm—Irving M. Fishman

[57] ABSTRACT

The invention relates to a process for the preparation of a compound of formula

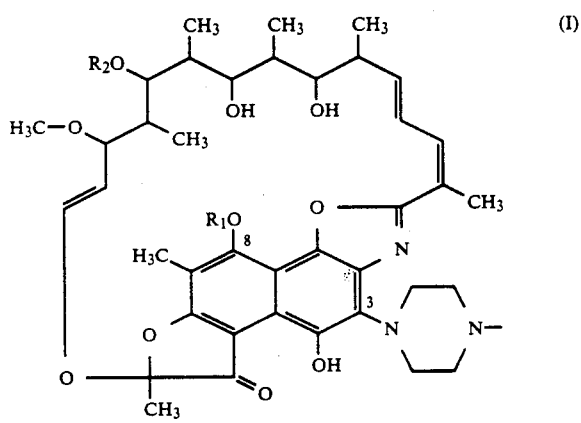

(I)

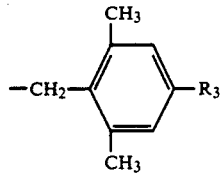

-continued or a salt thereof, wherein $R_1$ is hydrogen or trialkylacetyl, $R_2$ is hydrogen or acetyl and $R_3$ is alkyl, which process comprises cyclising a compound of formula

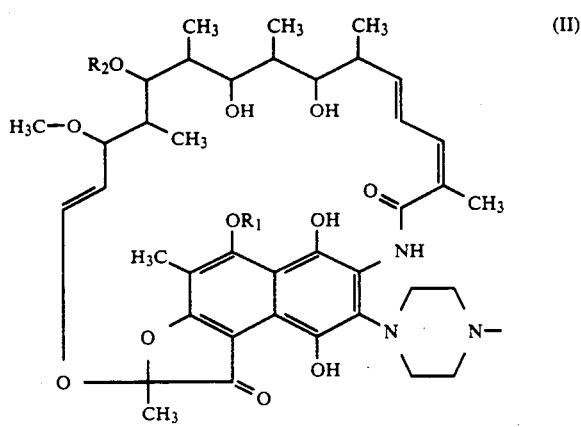

(II)

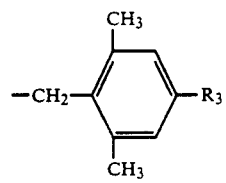

wherein $R_1$ is trialkylacetyl and, if desired, converting a compound of formula I obtainable by said process or in another manner, or a salt thereof, into another compound of formula I or a salt thereof, or converting a resultant free compound of formula I into a salt and/or a resultant salt into the free compound of formula I or into another salt.

10 Claims, No Drawings

PROCESS FOR THE PREPARATION OF POLYCYCLIC COMPOUNDS

The present invention relates to a novel process for the preparation of polycyclic compounds of formula

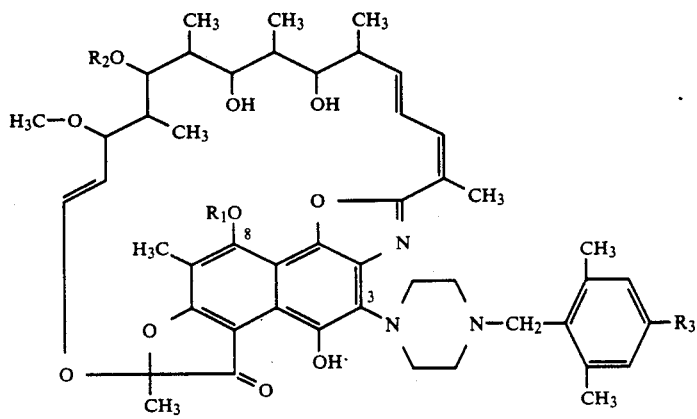

and the salts thereof, wherein $R_1$ is hydrogen or trialkylacetyl, $R_2$ is hydrogen or acetyl and $R_3$ is alkyl.

The numbering of the ring system corresponds to that used, for example, in U.S. Pat. No. 4,005,077.

The compounds of formula I and the salts thereof are disclosed in European patent application 0 314 624.

The compounds of formula I have several centres of chirality; hence the present invention also encompasses the corresponding optical isomers, for example diastereoisomers.

The compounds of formula I may also be obtained in the form of, preferably, pharmaceutically acceptable salts. As the eligible compounds of this invention contain basic centres, they are also able to form acid addition salts. These salts are formed with, for example, inorganic acids such as mineral acids, for example sulfuric acid, a phosphorus or hydrohalic acid, or with organic carboxylic acids such as unsubstituted or halogen-substituted $C_1$-$C_4$alkanecarboxylic acids, for example acetic acid, unsaturated or saturated dicarboxylic acids such as oxalic acid, malonic acid, succinic acid, maleic acid, fumaric acid, phthalic acid or terephthalic acid, hydroxycarboxylic acids such as glycollic acid, lactic acid, malic acid, tartaric acid or citric acid, amino acids such as aspartic acid or glutamic acid, or with organic sulfonic acids such as unsubstituted or halogen-substituted $C_1$-$C_4$alkanesulfonic or arylsulfonic acids, for example methanesulfonic acid, bromobenzenesulfonic acid or toluenesulfonic acid. Corresponding acid addition salts may also be formed with the additional basic centre. Further, the compounds of this invention containing an acid phenolic hydroxyl group can also form salts with bases, for example alkali metal salts such as sodium or potassium salts. Corresponding inner salts can also be formed.

Trialkylacetyl is preferably tri($C_1$-$C_7$)alkylacetyl, most preferably tri($C_1$-$C_4$)alkylacetyl, where alkyl is as defined below. Pivaloyl is most preferred.

Alkyl is preferably $C_1$-$C_7$alkyl and is typically methyl, ethyl, propyl, isopropyl, n-butyl, isobutyl, sec-butyl, tert-butyl and further encompasses in particular pentyl, hexyl and heptyl radicals. $C_1$-$C_4$Alkyl is preferred, but the most preferred meaning is methyl.

Derivatives which are derived, for example, from rifamycin SV are known to have pronounced antibiotic properties and can be used, for example, for the treatment of tuberculosis. It has been found that the compounds of formula I and the pharmaceutically acceptable salts thereof exhibit no corresponding antibiotic activity in the conventional pharmacological test models for clinical testing.

Surprisingly, however, they do have a significant lipid-lowering activity, which can be demonstrated in animal tests, preferably carried out on mammals, for example rats (cf. EP-A-314,624).

Especially on account of their LDL-lowering activity, the compounds of this invention can be used, for example, as hypolipidemic agents for the treatment of hyperlipidemia, mainly of types IIa and IIb, and atherosclerosis, for example when hyperlipoproteinemia is a risk factor.

Accordingly, the compounds of formula I and the pharmaceutically acceptable salts thereof can be used, for example, as pharmaceuticals, for example as hypolipidemic agents for the treatment of hyperlipidemia, mainly of types IIa and IIb, and of arteriosclerosis when hyperlipoproteinemia is a risk factor.

The invention relates in particular to compounds of formula I and salts thereof, wherein $R_1$ is pivaloyl and $R_3$ is methyl.

The invention relates more particularly to the mode of preparation described in the Examples.

The process for the preparation of the compounds of formula I and the salts thereof comprises cyclising a compound of formula

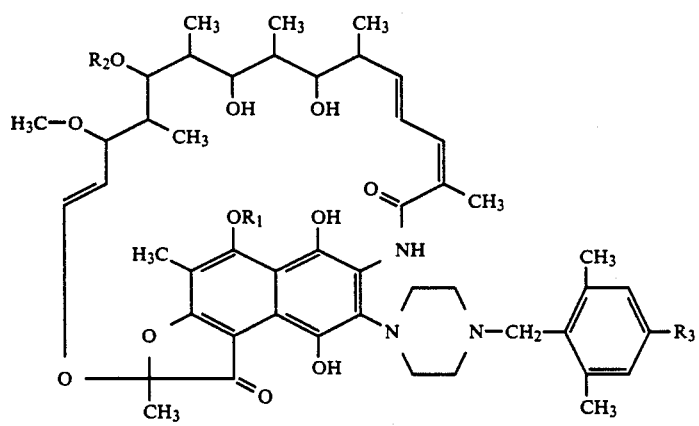

(II)

wherein $R_1$ is trialkylacetyl and, if desired, converting a compound of formula I obtainable by said process or in another manner, or a salt thereof, into another compound of formula I or a salt thereof, or converting a resultant free compound of formula I into a salt and/or a resultant salt into the free compound of formula I or into another salt.

Salts of the starting materials of formula II which contain an acid phenolic hydroxyl group are corresponding salts with bases of the indicated kind, whereas corresponding starting compounds having basic centres are also able to form corresponding acid addition salts in similar manner to the acid addition salts of formula I.

The reaction is carried out in a manner known per se, for example in the absence or, normally, in the presence, of a suitable solvent or diluent or mixture thereof, the process being carried out, if necessary, in a closed reactor under pressure, in an inert gas atmosphere and/or under anhydrous conditions.

The working up and isolation of the reaction product from the reaction mixture is effected in a manner known per se, for example by dilution with water and/or, if desired, by neutralisation or slight acidification (to about pH 3) with an aqueous acid, for example an inorganic or organic acid such as a mineral acid or, conveniently, citric acid, and addition of a water-immiscible solvent, such as a chlorinated hydrocarbon, for example chloroform or methylene chloride, whereupon the reaction product transfers to the organic phase from which it can be obtained in purified form in conventional manner, for example by drying, removing the solvent by evaporation, and crystallisation and/or chromatography of the residue or by other customary methods of purification.

$R_1$ is most preferably pivaloyl.

The cyclisation of compounds of formula II is conveniently effected with heating, for example in the temperature range from ca. 50° C. to the boiling temperature of the reaction mixture, for example up to ca. 180° C., the preferred temperature range being from ca. 100° C. to ca. 170° C.

It is preferred to obtain compounds of formula I, wherein $R_1$ is hydrogen, and to acylate these compounds by treatment with one of the acylating agents listed below, especially a pivaloyl halide, for example pivaloyl chloride.

The starting material of formula II can be prepared, for example, by reacting rifamycin S or 3-halorifamycin S, preferably 3-bromorifamycin S, with an amine of formula

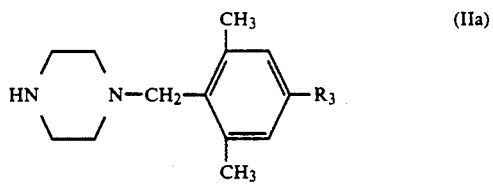

(IIa)

The process is carried out with an excess of amine of formula IIa, for example in the temperature range from ca. 0° C. to 100° C. A mixture of the quinone and hydroquinone form is obtained. This mixture can be converted into the corresponding hydroquinone (derivative of rifamycin S) ($R_1=1$) by reduction, for example by catalytic hydrogenation. Compounds of formula II, wherein $R_1$ is trialkylacetyl, can be obtained by treatment with a suitable acylating agent, for example an acid anhydride such as pivaloyl chloride, in the presence of a base such as pyridine.

The invention also relates to the novel compounds obtainable by the above process.

A compound of formula I obtainable by the process of the invention or in another manner, or a salt thereof, can be converted in a manner known per se into another compound of formula I.

Compounds of formula I, wherein $R_1$ is hydrogen, can be acylated in a manner known per se, for example by reaction with the appropriate carboxylic acid or a reactive derivative thereof. Such reactive derivatives are, for example, anhydrides, including mixed anhydrides such as an acid halide, for example an acid chloride, or anhydrides with an ester of formic acid, activated carboxylic acid esters such as cyanomethyl ester, 4-nitrophenyl ester, polyhalophenyl ester, for example pentachlorophenyl ester. The reaction with the carboxylic acid or a salt thereof is carried out with elimination of water, for example by removing the water of reaction as an azeotrope, or by treatment with a suitable condensing agent, for example N,N'-dicyclohexylcarbodiimide. The reaction with a reactive acid derivative is conveniently carried out in the presence of a base. Similarly, the acetyl radical $R_2$ can be introduced into compounds of formula I, wherein $R_2$ is hydrogen, by treatment with a suitable acylating agent, if necessary after reversibly protecting the OH groups at C-21 and C-23.

The acetyl radical $R_2$ and the acyl radical $R_1$ can be replaced by hydrogen by treatment with a strong base such as an alkali metal hydroxide. The acyl radical $R_1$ can also be removed selectively, in the presence of the acetyl radical $R_2$, for example by treatment with a fluoride such as an alkali metal fluoride, for example sodium or caesium fluoride, or with an ammonium fluoride, for example tetrabutylammonium fluoride.

Salts of compounds of formula I can be prepared in a manner known per se. Thus, for example, acid addition salts of compounds of formula I are obtained by treatment with an acid or with a suitable ion exchange reagent. Salts can be converted in customary manner into the free compounds; acid addition salts, for example, by treatment with a suitable base.

Depending on the mode of synthesis or on the reaction conditions, the compounds of the invention having salt-forming, especially basic, properties, can be obtained in the free form or, preferably, in the form of salts.

Because of the close relationship between the novel compounds in the free form and in the form of their salts, the references made throughout this specification to the free compounds and their salts also apply by analogy to the corresponding salts and free compounds.

The novel compounds, including their salts of salt-forming compounds, can also be obtained in the form of hydrates or include other solvents used for crystallisation.

Depending on the choice of starting materials and procedures, the novel compounds may be in the form of one of the possible isomers or as mixtures thereof, e.g. depending on the number of asymmetric carbon atoms they may be in the form of pure optical isomers such as antipodes or as mixtures of isomers, for example racemates, mixtures of diastereoisomers or mixtures of racemates.

Resultant mixtures of racemates can be separated in known manner into the pure isomers or racemates on the basis of the physico-chemical differences between the components, for example by fractional crystallisation. Resultant racemates can also be resolved into the optical antipodes by known methods, for example by recrystallisation from an optically active solvent, chromatography on chiral adsorbents, with the aid of microorganisms, by cleavage with specific immobilised enzymes, via the formation of inclusion compounds, for example using chiral crown ethers, such that only one enantiomer is complexed, or by conversion into diastereoisomeric salts, for example by reaction with a basic final racemate with an optically active acid such as a carboxylic acid, for example tartaric or malic acid, or a sulfonic acid such as camphorsulfonic acid, and separation of the resultant mixture of diastereoisomers, for example on the basis of their different solubilities, into the diastereoisomers from which the desired enantiomers can be isolated by treatment with suitable agents. It is advantageous to isolate the more active enantiomer.

The invention also relates to those embodiments of the process in which a compound obtainable as intermediate at any stage of the process is used as starting material and the remaining steps are carried out, or a starting material is used in the form of a derivative or salt and/or of its racemates or antipodes or, preferably, is formed under the reaction conditions.

In the process of this invention it is preferred to use those starting materials that lead to the compounds referred to at the outset as being especially useful. The invention further relates to the novel starting materials which have been specially developed for the preparation of the compounds of this invention, in particular novel compounds of formula III, their use, and processes for their preparation, the substituents $R_1$, $R_2$ and $R_3$ having the meanings given for the respective preferred groups of compounds of formula I.

The following Examples illustrate the present invention, but in no way limit the scope thereof.

EXAMPLE 1

A 10% solution of freshly prepared 8-O-pivaloyl-3-[4-(2,4,6-trimethylbenzyl)piperazin-1-yl]-rifamycin SV in toluene is heated in a pressure reactor to 170° C. for 15 minutes. The toluene is then removed by evaporation. The residue crystallises from methanol/water. The crystals which melt at 175° C., and which are obtained from two recrystallisations, are 1-desoxy-15-desoxo-1,15-oxy-3-[4-(2,4,6-trimethylbenzyl)piperazin-1-yl]-rifamycin of formula I, wherein $R_1$ is hydrogen, $R_2$ is acetyl and $R_3$ is methyl.

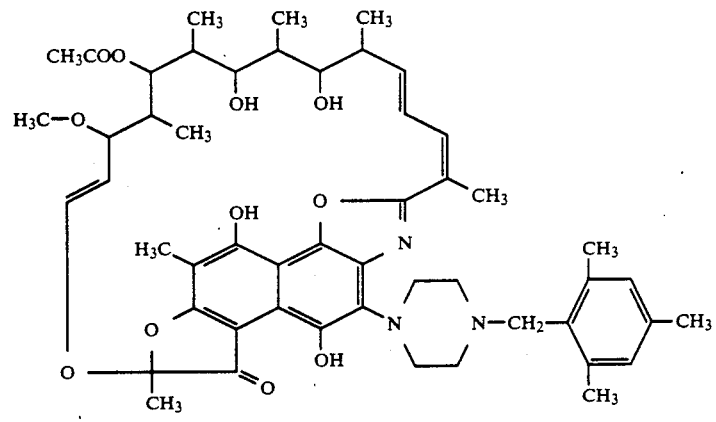

The starting material can be prepared as follows:

a) With stirring, 1.5 g of pivaloyl chloride (1.13 eq.) are added dropwise to a solution of 10 g of 3-[4-(2,4,6-trimethylbenzyl)piperazin-1-yl]-rifamycin S in 100 ml of pyridine, and the mixture is reacted for 10 minutes. Then 10 ml of methanol are added to the reaction mixture and stirring is continued for 1 hour. The reaction mixture is subsequently evaporated to dryness and the residue is dissolved in ethyl acetate. The ethyl acetate solution is washed with an aqueous solution of sodium hydrogencarbonate and a saturated solution of sodium chloride, dried over $Na_2SO_4$, and concentrated by evaporation. The residual 8-O-pivaloyl-3-[4-(2,4,6-trimethylbenzyl)piperazin-1-yl]-rifamycin S crystallises from ether in the form of bluish-black crystals which melt at 191°–193° C. (Z) (sintering at ca. 162° C., and also again at ca. 175° C.).

b) The resultant quinone is dissolved in tetrahydroquinone and, with good stirring, an excess of zinc dust is added to the solution, followed by the dropwise addition of 1N hydrochloric acid until the reaction mixture has turned yellow. The reaction mixture is filtered, and the tetrahydrofuran solution is washed twice with a saturated solution of sodium chloride, dried over sodium sulfate, and concentrated rapidly under vacuum at low temperature.

The yellow residue is 8-O-pivaloyl-3-[4-(2,4,6-trimethylbenzyl)piperazin-1-yl]-rifamycin SV, which can be used in this form direct for the cyclisation. The product crystallises from ether in the form of orange-yellow crystals which melt at ca. 165° C. with decomposition.

EXAMPLE 2

With stirring, 1.5 g of pivaloyl chloride are added dropwise to a solution of 10 g of 1-desoxy-15-desoxo-1,15-oxy-3-[4-(2,4,6-trimethylbenzyl)piperazin-1-yl]-rifamycin in 100 ml of pyridine, and the mixture is reacted at 20° C. for 10 minutes. Then 10 ml of methanol are added to the reaction mixture and stirring is continued for 1 hour. The reaction mixture is subsequently evaporated to dryness and the residue is dissolved in ethyl acetate. The ethyl acetate solution is washed with an aqueous solution of sodium hydrogencarbonate and a saturated solution of sodium chloride, dried over $Na_2SO_4$ and concentrated by evaporation, to give 8-O-pivaloyl-1-desoxy-15-desoxo-1,15-oxy-3-[4-(2,4,6-trimethylbenzyl)piperazin-1-yl]-rifamycin of formula I, wherein $R_1$ is pivaloyl, $R_2$ is acetyl, and $R_3$ is hydrogen, which melts at 160°–165° C.

What is claimed is:

1. A process for the preparation of a compound of formula

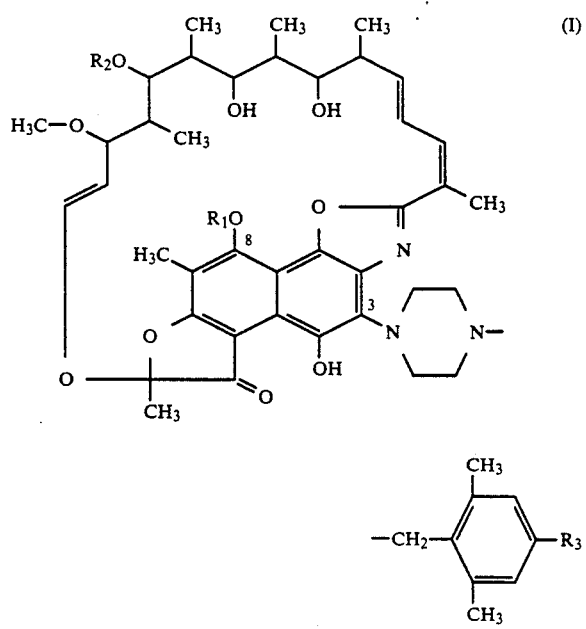

or a salt thereof, wherein $R_1$ is hydrogen or trialkylacetyl, $R_2$ is hydrogen or acetyl and $R_3$ is alkyl, which process comprises cyclising a compound of formula wherein $R_1$ is trialkylacetyl and, if desired, converting a compound of formula I obtainable by said process or in another manner, or a salt thereof, into another compound of formula I or a salt thereof, or converting a resultant free compound of formula I into a salt and/or a resultant salt into the free compound of formula I or into another salt.

2. A process according to claim 1, wherein the cyclisation is carried out in the temperature range from ca. 50° C. to the boiling temperature of the reaction mixture.

3. A process according to claim 3, wherein the cyclisation is carried out in the temperature range from ca. 50° C. to ca. 170° C.

4. A process according to claim 1, which comprises, for the manufacture of a compound of formula I, wherein $R_1$ represents trialkylacetyl, treating a resultant compound of formula I, wherein $R_1$ is hydrogen, with an acylating agent which corresponds to $R_1$.

5. A process according to claim 4, which comprises treating a resultant compound of formula I, wherein $R_1$ is hydrogen, with a pivaloyl halogenide, such as pivaloyl chloride.

6. A process according to claim 1 for the preparation of a compound of formula I or a salt thereof, wherein $R_1$ is tri($C_1$–$C_7$)alkylacetyl and $R_3$ is $C_1$–$C_7$alkyl.

7. A process according to claim 1 for the preparation of a compound of formula I or a salt thereof, wherein $R_1$ is tri($C_1$–$C_4$)alkylacetyl and $R_3$ is $C_1$–$C_4$alkyl.

8. A process according to claim 1 for the preparation of a compound of formula I or a salt thereof, wherein $R_1$ is pivaloyl and $R_3$ is methyl.

9. A process according to claim 1 for the preparation of 1-desoxy-15-desoxo-1,15-oxy-3-[4-(2,4,6-trimethylbenzyl)piperazin-1-yl]-rifamycin or a salt thereof.

10. A process according to claim 1 for the preparation of 8-O-pivaloyl-1-desoxy-15-desoxo-1,15-oxy-3-[4-(2,4,6-trimethylbenzyl)-piperazin-1-yl]-rifamycin or a salt thereof.

* * * * *